(12) United States Patent
Belfadhel et al.

(10) Patent No.: US 7,141,640 B2
(45) Date of Patent: Nov. 28, 2006

(54) PROCESS FOR PRODUCING DIHYDROXY COMPOUNDS USING UPFLOW REACTOR SYSTEM

(75) Inventors: Hatem Belfadhel, Bergen op Zoom (NL); Corinne Duchanoy, Rotterdam (NL); Jan-Willem Goedmakers, Putte (NL); Eduard Hendricus Schlarmann, Bergen op Zoom (NL); Monique I. R. de Winne, Middelburg (NL)

(73) Assignee: General Electric Company, Schenectady, NY (US)

( * ) Notice: Subject to any disclaimer, the term of this patent is extended or adjusted under 35 U.S.C. 154(b) by 138 days.

(21) Appl. No.: 10/065,357

(22) Filed: Oct. 8, 2002

(65) Prior Publication Data

US 2004/0068085 A1 Apr. 8, 2004

(51) Int. Cl.
*C08G 64/00* (2006.01)

(52) U.S. Cl. .................. 528/196; 208/210; 208/211; 208/212; 208/251; 210/521; 210/522; 585/510; 585/514

(58) Field of Classification Search ............. 208/210, 208/211, 212, 251; 210/521, 522; 585/510, 585/514
See application file for complete search history.

(56) References Cited

U.S. PATENT DOCUMENTS

| | | | |
|---|---|---|---|
| 3,785,779 A | 1/1974 | Li et al. | |
| 4,233,269 A | 11/1980 | Kaye et al. | |
| 5,395,857 A | 3/1995 | Berg et al. | |
| 5,985,135 A * | 11/1999 | Gupta | ......................... 208/212 |
| 6,013,845 A | 1/2000 | Allan et al. | |
| 6,033,635 A | 3/2000 | Gammill | |
| 6,086,749 A | 7/2000 | Kramer et al. | |
| 6,258,900 B1 | 7/2001 | Glover | |
| 6,309,553 B1 * | 10/2001 | Lanting et al. | ............. 210/802 |
| 6,554,994 B1 * | 4/2003 | Reynolds et al. | ........... 208/211 |

FOREIGN PATENT DOCUMENTS

WO    WO 00/50372    8/2000

* cited by examiner

*Primary Examiner*—Terressa Boykin

(57) ABSTRACT

An upflow reactor for the production of bisphenol A from acetone and phenol includes a vessel, a catalyst bed disposed within the vessel, and a reactant distribution/product collection system disposed within the vessel. The reactant distribution/product collection system includes a perforated distributor disposed at a lower end of the reactor. The reactant distribution/product collection system further includes a perforated collector disposed at an upper end of the reactor. A method for producing bisphenol A from acetone and phenol Includes Introducing the reacting mixture containing acetone and phenol to the distributor, directing it upward through the catalyst bed, and recovering the reacted acetone and phenol as bisphenol A together with other isomers and non reacted species. A method for avoiding catalyst bead carryover from the bed in an upflow reactor Includes receiving a product of the upflow reactor into the collector disposed at an upper end of the reactor through a screen with proper slit size.

28 Claims, 8 Drawing Sheets

PROCESS FOR PRODUCING DIHYDROXY COMPOUNDS USING UPFLOW REACTOR SYSTEM

BACKGROUND

This disclosure relates generally to a chemical reactor system for the production of dihydroxy compounds that minimizes pressure drop, channeling, and maldistribution of reactant and product flow through the bed of the reactor system. More particularly, the disclosure relates to the production of 2,2-bis(4-hydroxyphenyl)propane by introduction of a ketone and a phenol compound in an upflow mode from a reactant distribution system, direction of the reactants through a catalyst bed, and removal of products through a product collection system.

Dihydroxy compounds, and in particular bisphenols, are used as raw materials in the preparation of chemical products such as epoxy resins and polycarbonates. They are commonly prepared by the condensation of ketones and phenols. Typical bisphenols include 2,2-bis(4-hydroxyphenyl)propane (also known as bisphenol A, hereinafter BPA), which can be produced by reacting acetone (also known as dimethyl ketone) and a phenol in the presence of an acid.

A packed bed reactor system utilized in the production of bisphenols generally comprises a bed of packed materials such as, for example, catalyst that may be particulate in form (e.g., beaded), to which liquid reactants are introduced. The reactants are made to flow through the bed where they contact each other in the presence of the catalyst and react to form a final product and by products that is removed from a downstream point in the bed. In such packed bed reactor systems. pressure associated with the bed oftentimes has an effect on the physical of the reactor. Differential pressure, which is a measure of the resistance to flow over the height of the packed bed, increases with increased bed height. The differential pressure over the height of the packed bed may compress and deform the catalyst beads causing a reduction in liquid throughput as a result of pressure drop limitations. In response to an increase in the differential pressure, and because the density of the catalyst beads closely approximates the density of the liquid, fluid flow oftentimes suffers significant disruption, thereby resulting in a reduction of the throughput and/or "channeling."

The BPA reactors oftentimes operate in a down flow mode, where the exothermic condensation of phenol and acetone occurs in the presence of an acidic ion exchange resin (IER) catalyst and optionally in the presence of a co-catalyst promoter. When producing SPA in a downflow mode, the degree of cross-linking of certain IER catalysts directly affects the physical performance of the reactor as well as the reactivity, the selectivity, and the yield of this reactor. Indeed, Increasing the throughput of the BPA reactors operated in downflow configurations involves an increase in pressure drop and an increased risk that the beads will be misshapen and/or that the packed bed will collapse. Hydraulic limitations have also been observed particularly in the case of the IER catalyst having a low degree of cross-linking (e.g., less than or equal to about 2.5%). Although the hydraulic problems are less significant in IER catalysts having higher degrees of cross-linking, the reactivity, selectivity and life time (ton produced per ton of catalyst used) of such resins in the synthesis of BPA also decreases considerably. As such, a more highly cross-linked catalyst is generally more resistant to the hydraulic impact attributable to the particle shape and to the compression mechanism of the particle beads due to pressure. However, higher cross-linked catalyst also tends to be characterized by lower reactivity, lower selectivity, and shortened lifetime.

In an effort to compensate for the hydraulic limitations of catalysts having a lower degree of cross-linking while at the same time retaining the benefits of catalysts having a higher degree of cross-linking, BPA may be produced in a "combi-bed" apparatus, as is disclosed in U.S. Pat. No. 5,395,857 and U.S. patent application Ser. No. 09/258,235. The combi-bed apparatus optimizes the high production rate of BPA indicative of a catalyst having a high degree of cross-linking as well as the increased activity, selectivity, and lifetime of a catalyst having a lower degree (less than or equal to about 2% of cross-linking by combining both catalysts in the same reactor bed. Nevertheless, the capabilities of the combi-bed apparatus remain limited in terms of lifetime and in terms of maximum allowable throughput.

In further attempts to alleviate the problems associated with hydraulic limitations in catalyst beds, reactors have also been constructed to have an increased diameter while maintaining a decreased bed height, thereby allowing the reactors to utilize catalyst having a lower degree of cross-linking while operating with a pressure drop that enables acceptable reactor throughput to be maintained. In still further attempts to alleviate the problems associated with hydraulic limitations, reactants may be fed to BPA reactors in an upflow mode to reduce the effects of pressure drop on the performance of the reactors and to overcome throughput limitations.

Channeling is a condition of flow in which a fluid is permitted to randomly engage some active groups to the exclusion of other active groups. In channeled flow, portions of the bed may be short-circuited and not contacted by the fluid in a uniform and consistent manner. Such a condition can lead to the incomplete treatment or incomplete chemical reaction of the charged reactants. This, in turn, can result in the premature disposal of the catalyst or treatment particles, which translates into loss of part of the value of the catalyst.

Channeling may occur during the operation of a reactor in either the upflow mode or the downflow mode. In the upflow mode, the reactants are pressure-fed at a lower end of the reactor. As the reactants flow to the top of the reactor, they contact each other and the catalyst disposed in the reactor bed and react to form the desired product, which is retrieved from the top of the reactor. If the catalyst is in the form of beads, compression of the beads under their own weight causes a pressure drop to be realized over the height of the reactor. In the downflow mode, the reactants are fed to the top of the reactor. Pressure is typically applied to increase the reactant flow (and therefore the product takeoff rate). In the downflow mode, however, catalyst beads oftentimes compress under the action of the downward flow in addition to compressing under their own weight. Under compression, the catalyst beads may become misshapen and the packed bed may collapse thereby reducing the void fraction of the catalyst bed and magnifying the pressure drop issues.

Because of channeling and the resultant inefficient contact of the reactants with the catalyst, the operation of packed bed reactors is oftentimes significantly hindered, in particular, operations in which significant amounts of channeling occur generally result in low product yield, premature replacement of catalyst beds, and inefficient use of the reactants. This results not only in the cost of new catalyst, but also loss of production during outages, logistical costs of replacement, used catalyst disposal costs, and recovery and recycling of the reactants. Furthermore, a significant financial burden may be realized as a result of costs associated with efforts to improve catalyst technology. Such costs involve the development of alternate reactor geometries but not address the problem of existing reactors that have less favorable geometric features.

SUMMARY

An upflow reactor for the production of dihydroxy compounds is disclosed herein. The reactor includes a vessel, a catalyst bed disposed within the vessel, and a reactant distribution/product collection system disposed within the vessel. The reactant distribution/product collection system includes a distributor disposed at a lower end of the reactor and a collector disposed at an upper end of the reactor. Both the distributor and the collector each include a perforation. Screens are disposed over the perforations.

A method for producing a dihydroxy compound in an upflow reactor includes introducing a reactant to a distributor having a screen covered perforation disposed therein, directing the reactant from the distributor upward through a catalyst bed, and recovering the dihydroxy compound from an upper end of the upflow reactor.

A method for reducing the amount of catalyst bead carryover from a bed of catalyst beads in an upflow reactor includes receiving a product of the upflow reactor into a collector disposed at an upper end of the reactor, wherein the collector includes a perforation having a screen disposed thereat.

DETAILED DESCRIPTION

An apparatus for producing dihydroxy compounds (e.g., bisphenol isomers) and a method of use directed to the production of dihydroxy compounds are disclosed herein. The reactor includes a bed of catalyst through which the reactants flow to react and produce the final bisphenol isomers. The reactants flow in the generally vertical direction co-currently through the bed from a lower elevation to a higher elevation. To obtain favorable selectivity, yield, and reactant conversion, the reactor is designed such that a flow profile resembling or at least approximating plug flow can be achieved. Although the method is applicable to the production of any isomer of bisphenol, the preferred isomer is BPA produced by the reaction of a ketone (e.g., acetone) with a phenol in the presence of a catalyst and optionally in the presence of a co-catalyst (e.g., a reaction promoting agent). Typical phenols that may be utilized include, but are not limited to, ortho-cresol, meta-cresol, 2,6-dimethylphenol, ortho-sec-butylphenol, 1,3,5-xylenol, tetramethylphenol, 2-methyl-6-tertiary butylphenol, orthophenylphenol, ortho- and meta-chlorophenol, ortho-bromophenol, 2,6-dichlorophenol, and combinations of any of the foregoing phenols. The finished SPA product may be further combined with phosgene or diphenyl carbonate to produce a polycarbonate.

Figure 1:
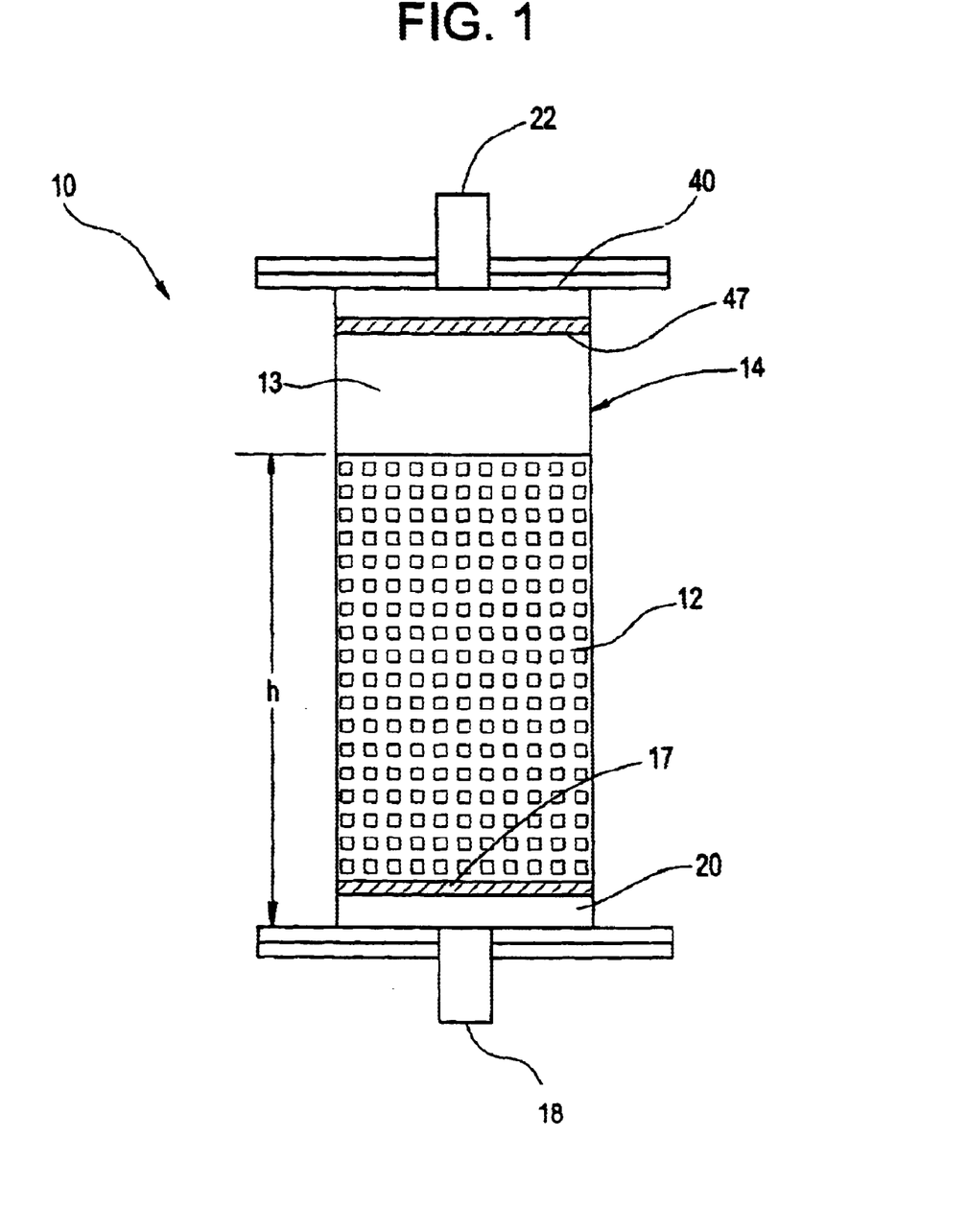
FIG. 1 is a schematic view of one exemplary embodiment of an upflow chemical reactor having a flat bottom.

Referring now to FIG. 1, one exemplary embodiment of an upflow chemical reactor utilized to produce the preferred bisphenol isomer is shown at 10 and is hereinafter referred to as "reactor 10." Reactor 10 includes a bed 12 comprising a catalyst and a reactant distribution/product collection system. Screens provide for the containment of the catalyst within the reacting area such that the reaction mixture can now through the system. A vapor space 13 may be defined above bed 12 in the upper part of reactor 10. The reactants acetone and phenol are directed in an upflow configuration through bed 12 to vapor space 13 via a distributor 20 of the reactant distribution/product collection system such that the maldistribution of flow (defined as the uneven dispersion of flow through a cross-sectional slice of the reactor) is minimized and a substantially uniform flow profile is maintained over any interstitial slice of bed 12. In order to minimize the amount of catalyst required for the most cost effective operation of reactor 10, bed 12 extends over a height h such that the product bisphenol isomer at the uppermost level of bed 12 is of the desired yield and selectivity.

The reactants are fed through distributor 20 such that channeling is substantially eliminated and plug flow is approximated. The elimination of channeling is indicated by a smooth temperature profile over height h of bed 12 and preferably over the full height of reactor 10. Temperatures can be measured at various points over the height of reactor 10 where they are recorded and evaluated to determine the reactant conversion profile and to evaluate if the proper flow profile is being maintained.

Figure 2:
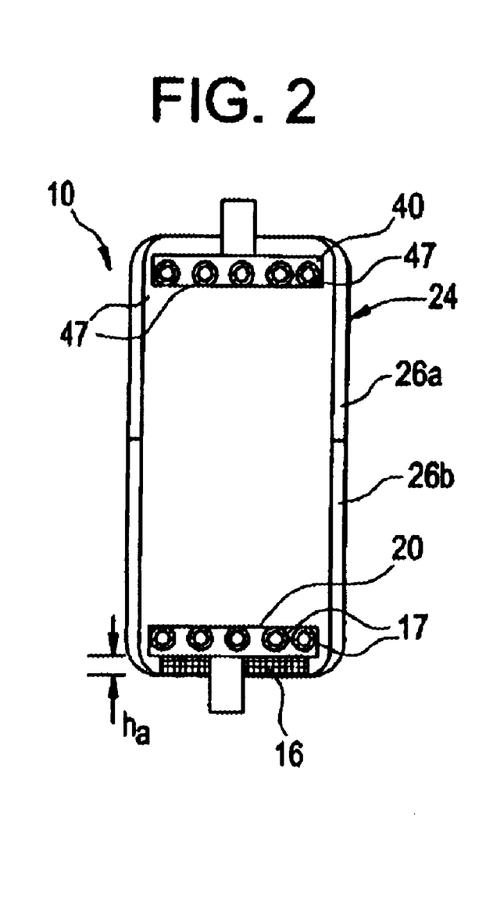
FIGS. 2 and 3 are schematic views of exemplary embodiments of upflow chemical reactors having non-flat bottoms.
Figure 3:
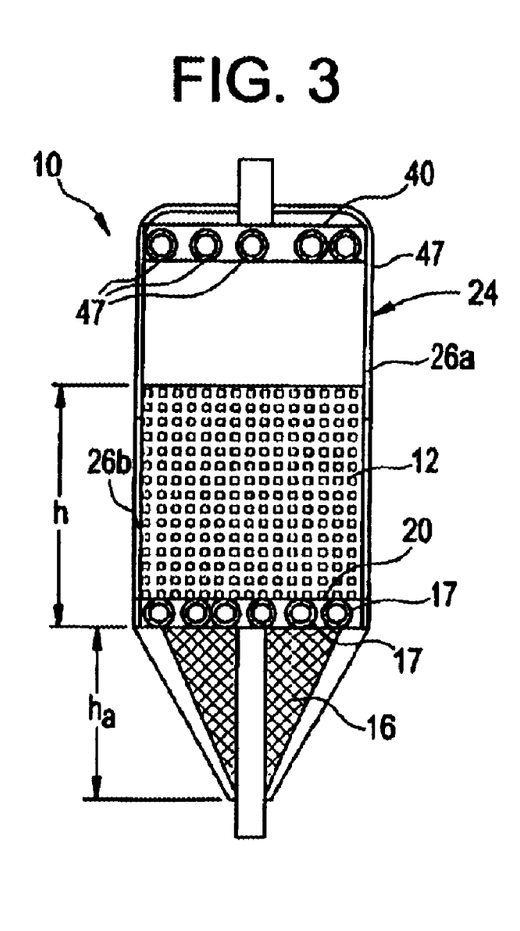

Bed 12 comprising the catalyst is contained by a vessel 14. Vessel 14 may be of any geometry capable of facilitating the flow of reactants in an upflow configuration. For example, vessel 14 may be substantially cylindrical, parallelepiped, or spherical in structure. Because cylindrically shaped vessels are widely available in the chemical industry, and because existing tanks or reactors can be converted into upflow reactors with relatively simple modifications, it is preferred that vessel 14 be of a cylindrical geometry. The lower end of vessel 14 is preferably flat (as shown in FIG. 1). The lower end may, however, be rounded (as shown in FIG. 2), conical (as shown in FIG. 3). or any combination of the foregoing configurations.

The catalyst disposed in vessel 14 is preferably at least a partially cross-linked ion exchange resin catalyst. The degree of cross-linking of the ion exchange resin catalyst is maintained at a level so as to preserve the integrity of the spherically shaped particles. In particular, the degree of cross-linking may be up to about 4%. Lower levels of cross-linking, however, Improve catalyst life, and therefore the degree of cross-linking is preferably about 2%. It is more preferred that the catalyst be a sulfonated aromatic resin containing some degree of divinylbenzene cross-linking and some degree of sulfonic acid functionality. The cross-linking density is most preferably equal to or below about 2.5%, and the acid milliequivalency is preferably greater than about 4 milliequivalents per gram (Meq/g). Optionally, co-catalysts may also be used. Typical co-catalysts (which may or may not be attached) include, but are not limited to, thiols and mercaptans.

Distributor screens may be disposed at any point intermediate distributor 20 and the outlet end of vessel 14. As shown in FIG. 1, a distributor screen (hereinafter described as "screen 17") preferably comprises mesh material or a flat plate that substantially corresponds to the cross sectional geometry of vessel 14 and is placed directly above distributor 20. Alternately, screen 17 may be a discrete mesh structure that individually wraps the arms of distributor 20, as is shown in FIGS. 2 and 3. In either embodiment, the size of the openings in screens 17 are about ⅖ to about one quarter of the size of the minimum particle diameter of the catalyst beads in the reaction mixture, with less than one third of the minimum diameter being preferred in order to discourage the receiving of the catalyst particles in distributor 20. For a catalyst having a partide size of about 400 micrometers to about 800 micrometers in diameter, the openings in screens 17 are about 100 micrometers to about 160 micrometers with less than 133 micrometers being preferred.

A packing material (not shown) may optionally be disposed within vessel 14 and interspersed within the catalyst. The packing material, which is generally rigid, bears the weight of the catalyst with which the packing material is interspersed, thereby affording the catalyst additional structural support within bed 12 by inhibiting the compression of the catalyst under its own weight. Because of the difficulties encountered by the separation of the catalyst from the packing materials, packing materials are generally used only with catalysts having low cross-linking. A typical packing material comprises a plurality of discrete objects dumped within the vessel of a reactor resulting in a random arrangement of surfaces and providing tortuous paths for the flow of the reactant materials. The objects may be fabricated from any rigid, chemically inert, and thermally stable material that allows for optimum contact of the reactant materials with each other and with the catalyst as they flow through the bed. Optimum contact is generally realized by objects having large void fractions (objects that are small in volume and have large surface areas). Preferred packing materials include, but are not limited to, Pall rings, Tellerette rings, Raschig rings, Berl saddles, Intalox saddles, and combinations of at least one of the foregoing packing materials.

An inlet 18 is disposed at a lower end of bed 12 to facilitate the introduction of the reactants to reactor 10. Inlet 18 may be a node at which tubing, piping, jets, or similar devices form a juncture that allows for the flow of reactants into the reaction zone defined by bed 12. Preferably, inlet 18 receives the reacting mixture and directs it into bed 12 through a distributor 20 of the reactant distribution/product collection system to produce the desired bisphenol A. An outlet 22 is disposed at an upper end of bed 12, directly in bed 12, in vapor space 13, or in a combination thereof.

Outlet 22 provides for the removal of the product isomer from reactor 10 by receiving the isomer through a collector 40.

Vessel 14 may further comprise a jacket 24 disposed at an outer surface thereof, as is shown in FIG. 2 and 3. jacket 24 may comprise a single zone that limits the amount of heat loss through the reactor wall. Alternately, jacket 24 may comprise two or more zones 26a, 26b, each of which are disposed in communication with a fluid source (not shown) that can provide either heating or cooling to bed 12 depending upon the desired operating temperature of reactor 10. Fluids that may be used to provide heat to bed 12 include, but are not limited to, steam, hot oil, or hot liquid streams, e.g., process waste streams. Fluids that may be used to provide cooling to bed 12 include, but are not limited to, refrigerants, brines, water, and the like. Alternatively, heating may be performed via electrically resistive elements disposed at the outer surface of the vessel.

Figure 4:
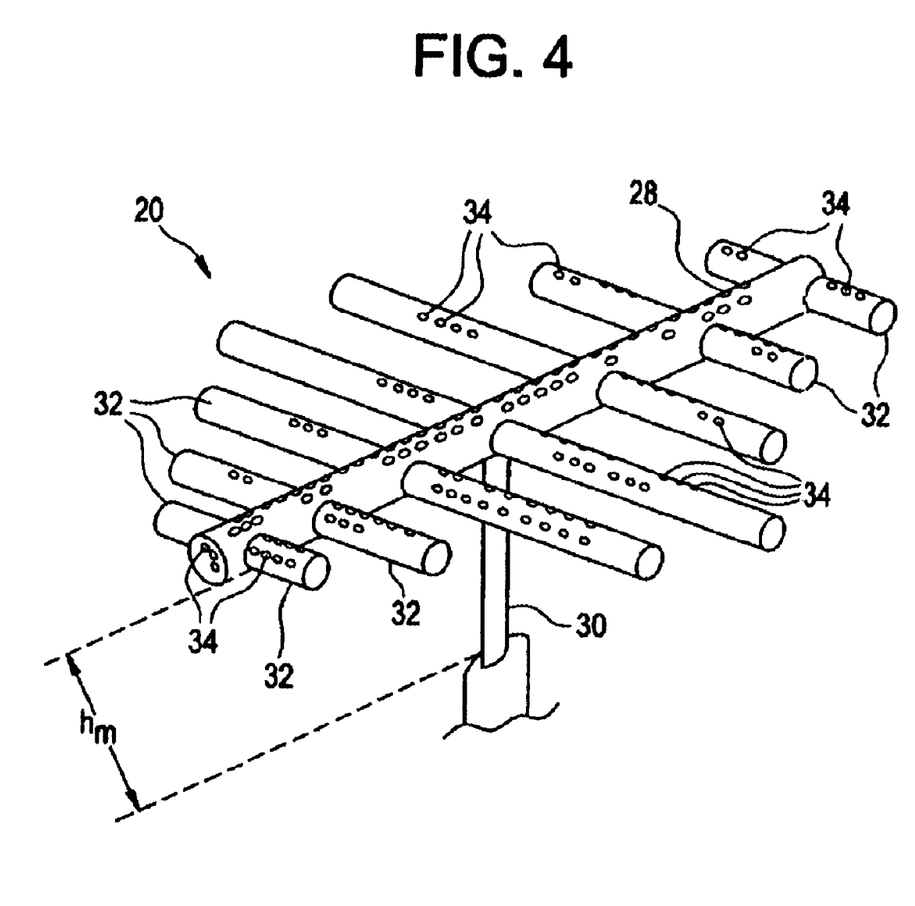
FIG. 4 is a perspective view of a reactant distributor.

FIG. 4 shows an example of configuration that provides a uniform distribution of the reaction mixture across the section of the reactor. Distributor 20 comprises a manifold 28 into which reactant material is received through a manifold inlet 30 disposed in fluid communication with the inlet of the reactor. In one exemplary embodiment of distributor 20, distribution arms 32 extend laterally from manifold 28. Distribution arms 32 disposed proximate opposing ends of manifold 28 are generally dimensioned to be shorter than the arms disposed proximate the center of manifold 28. As such, the outer defining edges of distributor 20 preferably corresponds to the cross sectional geometry of a cylindrical reactor. In particular, if the cross sectional dimension of the reactor is round, distribution arms 32 are generally dimensioned such that the outer ends of each extend from the inner surface of the reactor approximately the same distance to cause distributor 20 to approximate a circular shape when installed into the reactor and viewed from the upper- or lower end of the reactor.

If an aggregate layer (described below) is used as a bottom support for the catalyst bed, it is preferred to minimize contact between the reactants and the aggregate and to maximize contact between the reactants and the catalyst. Manifold inlet 30 is thus appropriately dimensioned such that distributor 20 is positioned within the reactor at the interface of the aggregate layer and the catalyst. Furthermore, in order to minimize the extent of undesirable side reactions affected by the reaction of the reactants with each other not in the presence of the catalyst. It may be desirable to maintain a height $h_m$ of inlet manifold (as well as the lengths of manifold 28 and distribution arms 32) as short as possible while still providing for sufficient distribution of the reactants across the cross sectional geometry of the reactor.

Manifold 28, as well as distribution arms 32, are preferably fabricated of piping having perforations 34 that enable fluid communication to be maintained between inlet manifold 30 and the catalyst disposed in the reactor bed.

Aggregate layers, as shown at 16 in FIGS. 2 and 3, may optionally be disposed at a lower end of bed 12. Aggregate layers 16 provide support to bed 12 and comprise a material that is essentially inert to the reactants and products produced in reactor 10. The material that comprises aggregate layer 16 may be, but is not limited to, silica sand, diatomaceous earth, ceramic balls, and combinations of the foregoing materials.

In reactors in which the bottom is not flat, the reactor is charged with aggregate layer 16 to a height $h_a$ that coincides with the height of the bottommost surface of the manifold of distributor 20. The catalyst is disposed on the top of distributor 20 to form the bed height h (FIG. 3). Height h is determined from experimental data obtained from laboratory and/or pilot plant trial runs to provide the maximum yield of the reaction as well as a reasonable frequency of catalyst changeovers. Accurate measurements of height h may be obtained by direct measurements through windows disposed along the height of the reactor.

Figure 5:
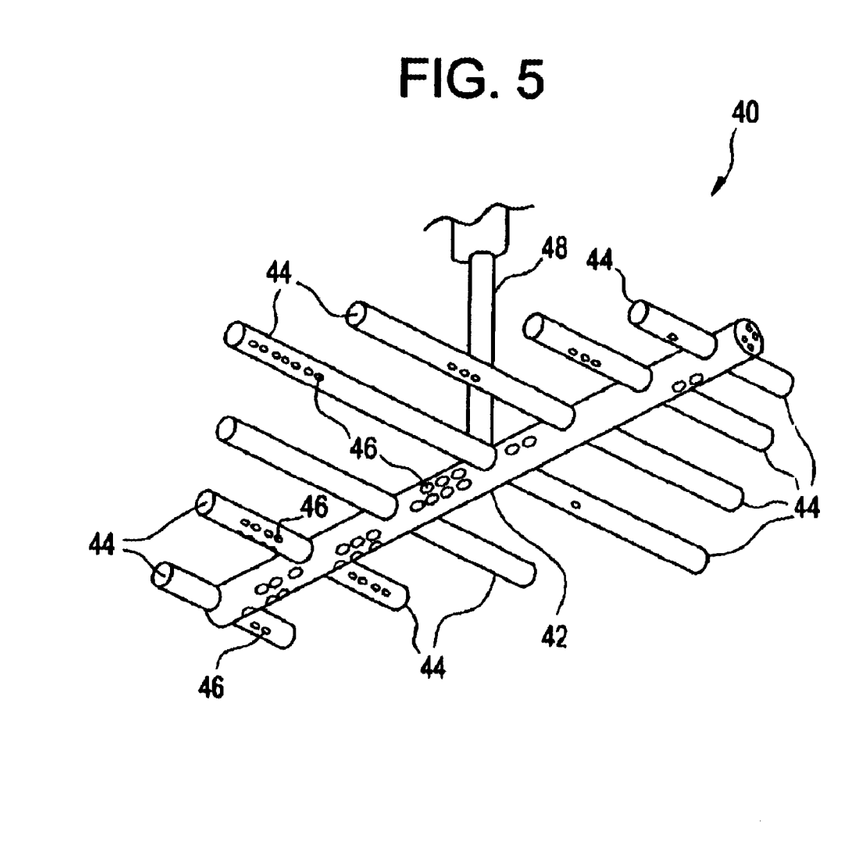
FIG. 5 is a schematic view of a product collector.

Referring now to FIG. 5, collector 40 is shown. Collector 40 is similar in structure to the distributor shown with reference to FIG. 4 and operates to reduce problems associated with dead volumes that could appear when flow out of the reactor is reduced from the bed to the effluent pipeline. It also allows good distribution of fluids in case the downflow mode has to be applied to the vessel. Collector 40 is positioned proximate the upper end of the reactor in fluid communication with the outlet of the reactor. Reaction products (e.g., SPA and isomers) produced from the reaction of acetone and phenol (as well as non-reacted components) are removed from the reactor system through collector 40.

Collector 40 comprises a manifold 42 having collection arms 44 extending therefrom. Collection arms 44, as well as manifold 42 include perforations 46 such that product bisphenol A can be received therein and removed through a product takeoff line 48. In one exemplary embodiment of collector 40, collection arms extend laterally from manifold 42. Collection arms 44 disposed proximate opposing ends of manifold 42 are generally dimensioned to be shorter than the arms disposed proximate the center of manifold 42. As such, the outer defining edges of collector 40 may correspond to the cross sectional geometry of a cylindrical reactor. As with the distributor, the ends of collection arms 44 may approximate the geometry of the inner surface of the reactor.

Referring to FIGS. 1–3, collector screens 47 may be disposed at any point intermediate distributor 20 and collector 40. Screens 47 preferably comprise mesh material or flat plates that substantially correspond to the cross sectional geometry of vessel 14 and are placed directly below collector 40, as is shown in FIG. 1. Alternately, screens 47 may be discrete mesh structures that individually wrap the arms of collector 40 as is shown In FIGS. 2 and 3. In either embodiment, the size of the openings in screens 47 are about ⅔ to about one quarter of the size of the minimum particle diameter of the catalyst beads in the reaction mixture, with less than one third of the minimum diameter being preferred in order to discourage the receiving of the catalyst particles in collector 40. For a catalyst having a particle size of about 400 micrometers to about 800 micrometers in diameter, the openings in screens 47 are about 100 micrometers to about 160 micrometers with less than 133 micrometers being preferred.

Particle entrainment outside the reaction section typically comprises catalyst carryover from the bed into product takeoff line 48. Catalyst carryover may take the form of either the removal of substantially fully intact beads from the bed or the removal of broken catalyst beads (fines) from the bed. Screens 47 disposed over collector 40) prevent or limit carryover of either the fully intact beads or the fines into takeoff line 48.

Operation of reactor 10 is described with reference to FIGS. 1–5. The reacting mixture comprising acetone and fresh and/or recycled phenol is introduced to reactor 10 through manifold inlet 30. The operation of the reactor may be "single-pass," e.g., the acetone and phenol may be fed to the reactor and the bisphenol and excess reactants removed at the reactor outlet. Preferably, however, the operation of the reactor includes a recirculation loop, e.g., the bisphenol is removed at the reactor outlet and the excess acetone and phenol are recycled back to the reactor feed. The pressure at which the reactants are introduced is sufficient to force the reactants out of distributor 20, through the catalyst of bed 12, and to collector 40. The composition of the fed reactants is monitored to ensure that proper specifications are met for the production of the desired bisphenol isomer. Monitoring of the reactants may be either inline or by the removal of samples from the inlet streams.

Temperature and pressure are monitored at inlet 18, at various points within bed 12, at vapor space 13 (if any), and at outlet 22. Flow rates may also be monitored. If the operation of reactor 10 is automated, the measurements can be utilized to control the feed rates of the reactants to inlet 18, as well as other parameters of the system.

It is preferred that the temperature on the top of the catalyst bed 12 be higher than the BPA crystallization temperature. In order to obviate the problems associated with the crystallization of product, or in case the reactor insulation is not sufficient, reactor 10 may be heated, particularly at the top portion thereof, by passing a hot fluid stream through jacket 26a. The hot fluid stream passed through Jacket 26a transfers heat to the reaction mixture and prevents bisphenol A crystallization.

EXAMPLE 1

A production run in which bisphenol A was produced from the reaction of acetone and phenol contained in a reaction mixture is described and shown with reference to FIGS. 6 through 10. The product bisphenol A was produced in a test reactor system, shown at 200 and hereinafter referred to as "system 200," comprising one test reactor and one safety vessel to collect carried over catalyst beads. Each vessel was 50 centimeters (cm) (19.7 inches (in.)) in diameter. The reactor was 5 meters (16.4 feet) in height). The first vessel, shown at 210 in FIG. 6, was configured to receive the reactants in an upflow mode and was substantially similar in structure to reactor 10 described with reference to FIGS. 1 through 5. In the initial run of system 200, first vessel 210 did not incorporate a distributor/collector system. First vessel 210 did, however, incorporate a screen in the bottom of the reactor. The screen mesh was such that the size of the openings in the screen were less than 100 micrometers (about one third of the minimum catalyst particle diameter). The second vessel, shown at 211, was disposed in serial fluid communication with an outlet of first vessel 210 at an upper end thereof through a jumper line 215. Second vessel 211 included a sand layer 217 disposed over a screen. First vessel 210 was charged with approximately 1 m$^3$ (cubic meter) (35.3 cubic feet (ft$^3$)) of wet catalyst to form a bed 212. The height of bed 212 was measured using direct observation to be 2.96 m (9.71 ft) when no liquid was flowing in vessel 210.

Figure 6:
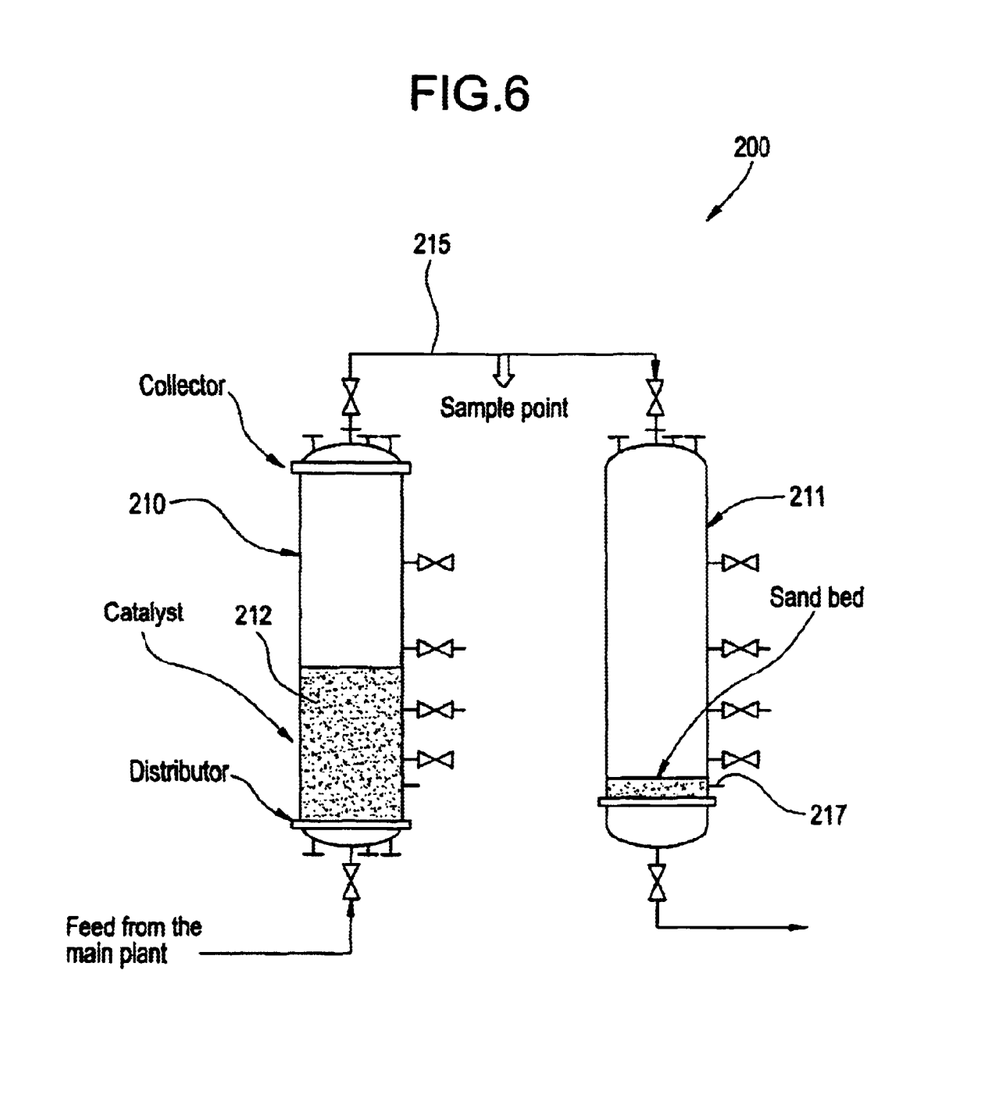
FIG. 6 is a schematic diagram of a test reactor system.
Figure 7:
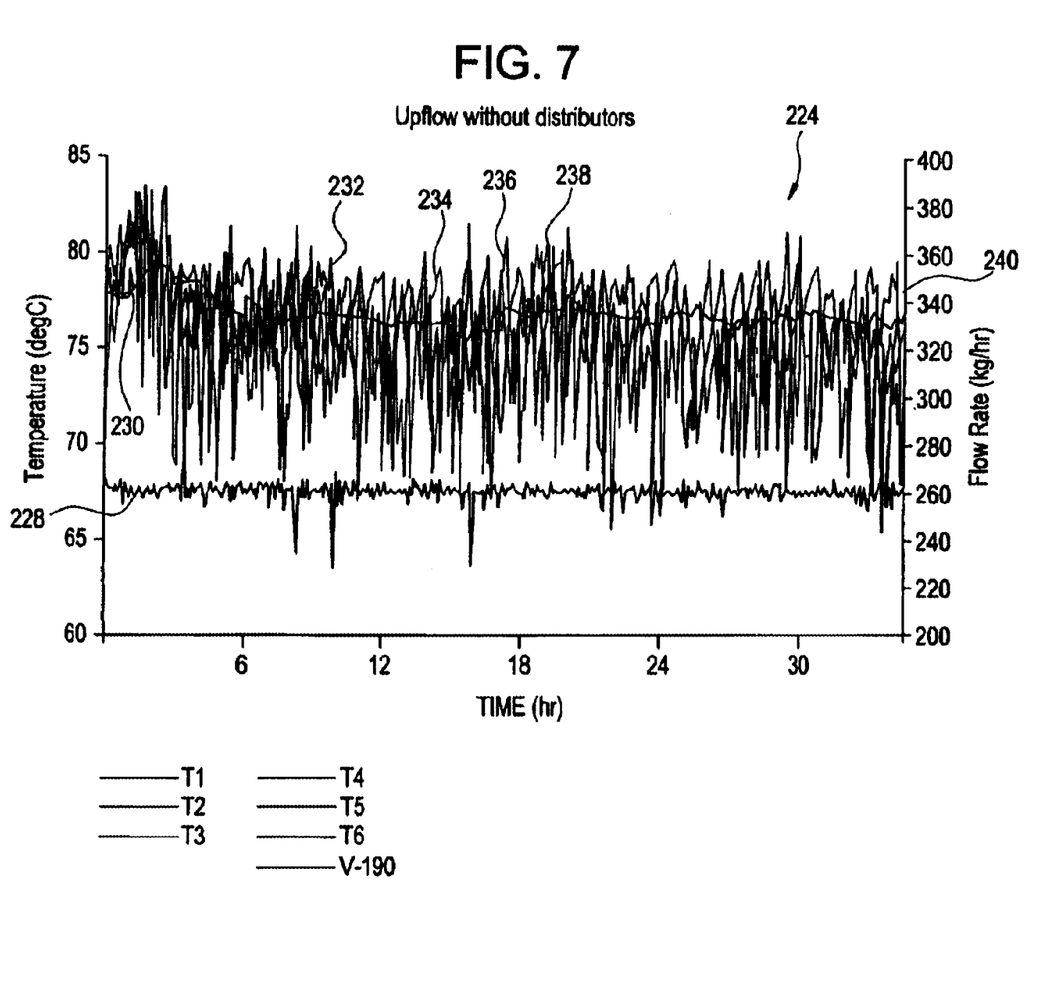
FIG. 7 is a graphical representation of temperature as a function of time in a test reactor system in which a distributor/collector system is not incorporated.

Six temperature probes were disposed within bed 212 and at various heights of first vessel 210. Referring now to FIG. 7, a graphical representation of the temperature profile of the initial run of system 200, as was described with reference to FIGS. 6, is shown at 224. The system was operated in which temperatures were monitored for a substantially constant reactant flow rate of approximately 260 kilograms per hour (kg/hr) (572 pounds per hour (lbs/hr)), shown at line 228. As can be seen from the temperature curves, temperatures sensed by the upper five temperature probes and plotted as lines 232, 234, 236, 238, and 240 experienced wide fluctuations in temperature over the height of the first reactor. Only the temperature probe positioned at the lowest level proximate the inlet of the first reactor recorded substantially stable temperature readings (plotted as line 230) that varied from about 65° C. to about 85° C. with a standard deviation of about 5° C. proximate the first temperature probe and about 1.6 C proximate the third probe for a space velocity of about 1.6 to about 1.7. Such a wide variation in temperature over the height of the first reactor indicates channeling and non-plug flow throughout the bed and the reactor. This was confirmed by the visual observation of the surface of the catalyst bed, which was not flat. Moreover, crystals of bisphenol A could be seen through the windows of the reactor at their inner surface, showing the presence of cold spots, and therefore the absence of plug-flow behavior.

EXAMPLE 2

Figure 8:
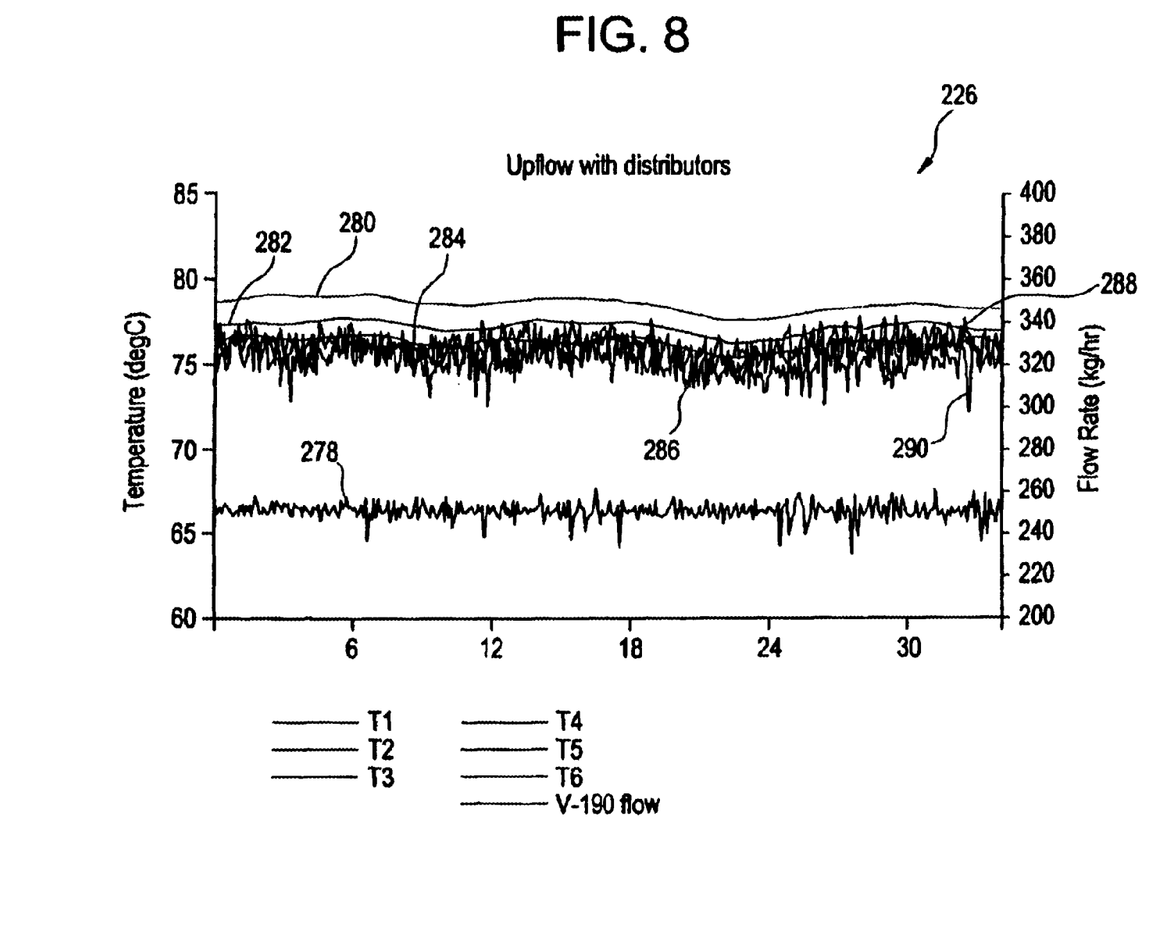
FIG. 8 is a graphical representation of temperature as a function of time in a test reactor system in which a distributor/collector system is incorporated.

A second run of system 200 was made in which a distributor/collector system similar to that described above with reference to FIG. 6 was operably mounted within the first reactor. Referring now to FIG. 8, a graphical representation of the temperature profile of the second run of system 200 is shown at 226. Temperatures were monitored at the same locations as in the first run for a substantially constant reactant flow rate of approximately 250 kg/hr (550 lbs/hr), shown at line 278. In the second run, the height of the bed was again measured to be 2.96 m (9.71 ft). The interface between the bed and the vapor space above the bed is intermediate the third and fourth temperature probes. As can be seen from the graphed data, the temperatures monitored by the lower three temperature probes provide constant temperature readings (lines 280, 282, and 284) over the run, while the upper three temperature probes provide temperature readings (lines 286, 288, and 290) in which the fluctuation is greatly improved over the temperature fluctuation of the first run. Because of the reduced amount of temperature fluctuation in the second run, and because of the observed flat surface of the catalyst bed, it can be concluded that the distributor/collector system substantially reduces the amount of channeling within system 200. For a space velocity of about 1.6 to about 1.7, the standard deviation is about 0.7° C. proximate the first probe and about 0.4° C. proximate the third probe.

Figure 9:
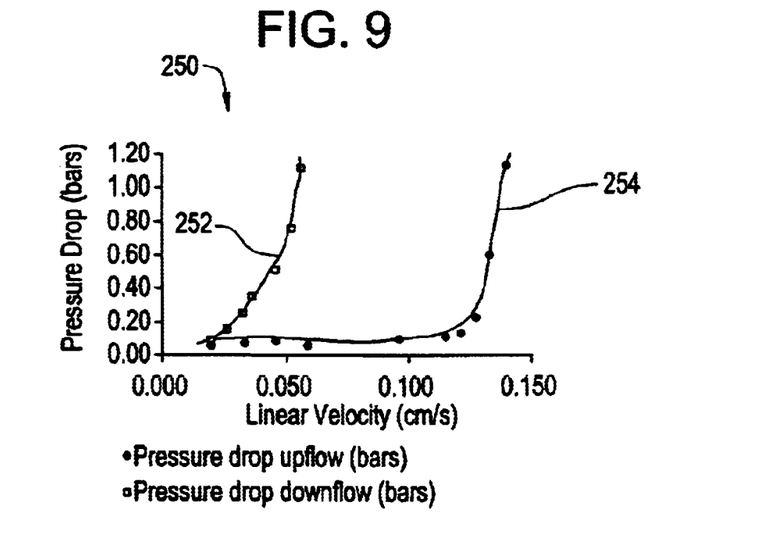
FIG. 9 is a graphical representation of pressure profiles in which pressure differentials are shown as functions of linear velocities for test reactor systems operating in both downflow and upflow modes.

In FIG. 9, pressure drop as a function of linear velocity of the reactants is presented graphically at 250. For a reactor configured to run in a downflow mode, the reactor reaches the pressure differential limit of 1 bar (14.5 pounds per square inch (psi)) at a linear velocity of about 0.057 cm/sec (0.022 in/sec), as indicated by a line 252. When the same reactor incorporating the distributor/collector system is run in an upflow mode, the pressure differential of 1 bar (14.5 psi) is attained at about twice the linear velocity (0.115 cm/sec (0.045 in/sec)) of the reactant flow, as indicated by a line 254. The sharp increase in the pressure differential beyond the linear flow rate of about 0.115 cm/sec (0.045 in/sec) is due to the packing of catalyst beads at the top of the bed of the reactor just below the collector. This physical limitation is due at least in part to the available free height on the top of the catalyst beads. For taller vessels, this sharp increase may occur for greater linear velocities. The differences between lines 252 and 254 illustrate the disparity in pressure drop across a reactor having a distributor/collector system operating in an upflow mode and a reactor having a distributor/collector system operating in a downflow mode.

Figure 10:
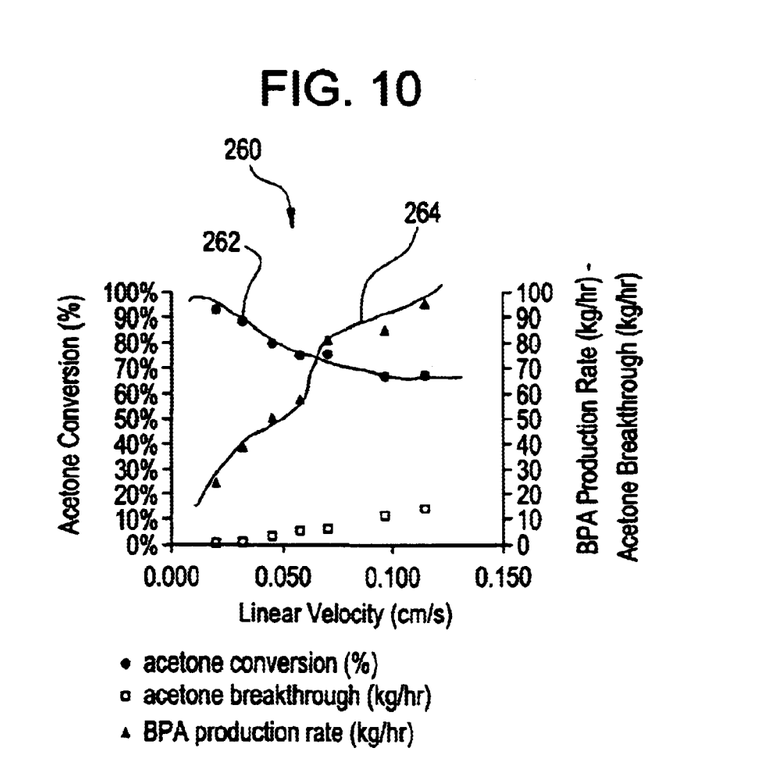
FIG. 10 is a graphical representation of acetone conversion and bisphenol A production as functions of the linear velocity.

In FIG. 10, the acetone conversion and the bisphenol A production rate are graphically presented as functions of the linear velocity of the reactants at 260. The acetone conversion decreases at high flow rates due to the reduction of the average residence time and the average catalyst concentration in the reactive volume, as can be seen by a line 262. The acetone breakthrough correspondingly increases, as can be seen by a line 264. The bisphenol A production throughput. However, increases because of the higher flow rate (linear velocity).

For all flow rates studied, the selectivity of the reaction of acetone and phenol to produce bisphenol A remained over 95%. No trend in selectivity behavior was detected because all data obtained was within 0.5%. The upflow reactor system incorporating the distribution/collection system described above provides several advantages over both upflow- and downflow systems currently in use. Minimization of the maldistribution of flow provides at least two advantages. First, it ensures that the catalyst bed is fully utilized, i.e., the maximum amount of catalyst is contacted by the reactants during their flow over the height of the reactor bed. Optimum performance of the reactor can then be achieved in terms of reactant conversion, selectivity, pressure drop, and bed stability. Second, it allows the reactor to be operated at higher feed rates, thereby enabling increased production rates to be realized. By providing for a more even distribution of cross-sectional flow over the height of the reactor, channeling is reduced, even for high linear velocity feed rates.

Another advantage of incorporating the distribution/collection system described above is that the reactor system has the capability of effectively operating with a broader range of catalysts. The distribution/collection system can accommodate catalysts having different characteristics in terms of density, particle size, and variations in particle size distributions. Furthermore, the distribution/collection system enables the efficient use of catalysts having lower degrees of cross-linking, which have the advantages of higher reactivity, better selectivity and longer lifetime.

Other advantages that may be realized include cost savings as a result of higher production rates and less frequent catalyst changeouts.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, It is intended that the disclosure not be limited to the particular embodiment disclosed as the best mode contemplated for carrying out this disclosure, but that the disclosure will include all embodiments falling within the scope of the appended claims.

What is claimed is:

1. An upflow reactor for producing dihydroxy compounds, said upflow reactor comprising:
   a vessel;
   a catalyst bed disposed in said vessel; and
   a reactant distribution/product collection system disposed in said vessel, said reactant distribution/product collection system comprising,
      a distributor in fluid communication with an inlet through which reactants are introduced to said distributor, said distributor being disposed at a lower end of said vessel and comprising a perforation disposed in said distributor and a first screen disposed at said perforation in aid distributor, and
      a collector through which said product dihydroxy compound is removed, said collector being disposed at an upper end of said vessel and comprising a perforation disposed in said collector and a second screen disposed at said perforation in said collector.

2. The upflow reactor of claim 1, further comprising an aggregate layer at said lower end of said vessel to support said catalyst bed.

3. The upflow reactor of claim 2, wherein said aggregate layer comprises silica sand, diatomaceous earth, ceramic balls, or a combination of the foregoing materials.

4. The upflow reactor of claim 1, wherein said vessel comprises a vessel having a structural geometry that is substantially cylindrical, substantially parallelepiped, substantially spherical, or a combination thereof.

5. The upflow reactor of claim 1, wherein said vessel further comprises a jacket disposed at an upper surface of said vessel.

6. The upflow reactor of claim 1, wherein said catalyst bed comprises a cross-linked ion exchange resin catalyst.

7. The upflow reactor of claim 1, wherein said distributor further comprises a plurality of perforated arms extending laterally from said perforated manifold.

8. The upflow reactor of claim 7, wherein said perforated arms disposed at opposing ends of said manifold are shorter than said perforated arms disposed intermediate said opposing ends of said manifold.

9. The upflow reactor of claim 1, wherein said collector further comprises a plurality of perforated arms extending laterally from said perforated manifold.

10. The upflow reactor of claim 9, wherein said perforated arms disposed at opposing ends of said manifold are shorter than said perforated arms disposed intermediate said opposing ends of said manifold.

11. The upflow reactor of claim 1, wherein said dihydroxy compound is a bisphenol.

12. The upflow reactor of claim 11, wherein said bisphenol is 2,2-bis(4-hydroxyphenyl)propane.

13. A distributor for an upflow reactor, said distributor being disposed at a lower end of said upflow reactor and comprising:

a manifold in fluid communication with an inlet into which a reactant is received;

a perforation disposed in said manifold; and a screen disposed at said perforation, said screen and said perforation being configured to allow said reactant to be communicated therethrough.

14. The distributor of claim 13, further comprising a plurality of arms extending from said manifold.

15. The distributor of claim 14, further comprising perforations disposed on said arms.

16. The distributor of claim 14, wherein said arms disposed proximate opposing ends of said manifold are shorter than said arms disposed intermediate said opposing ends of said manifold.

17. A collector for an upflow reactor, said collector being disposed at an upper end of said upflow reactor and comprising:

a manifold;

a perforation disposed in said manifold; and a screen disposed at said perforation, said screen and said perforation being configured to allow a product to be received in said manifold.

18. The collector of claim 17, further comprising a product takeoff line disposed in fluid communication with said manifold.

19. The collector of claim 17, further comprising a plurality of arms extending from said manifold.

20. The collector of claim 19, wherein said arms disposed proximate opposing ends of said manifold are shorter than said arms disposed intermediate said opposing ends of said manifold.

21. A method for producing a dihydroxy compound in an upflow reactor, said method comprising:

introducing a reactant to a distributor at a lower end of said upflow reactor, said distributor having a plurality of screen-covered perforations disposed therein;

directing said reactant from said distributor upward through a catalyst bed; and recovering said dihydroxy from an upper end of said upflow reactor.

22. The method of claim 21, wherein said recovering of said dihydroxy compound comprises receiving said compound through a collector disposed at said upper end of said upflow reactor, said collector having a plurality of screen-covered perforations disposed therein.

23. The method of claim 21, wherein said dihydroxy compound is a bisphenol.

24. The method of claim 23, wherein said bisphenol is 2,2-bis(4-hydroxyphenyl)propane produced from a ketone and a phenol.

25. A method for reducing the amount of catalyst bead carryover from a bed of catalyst beads in an upflow reactor, said method comprising: receiving a product of said upflow reactor into a collector disposed at an upper end of said upflow reactor, said collector having a plurality of perforations with screens disposed over said perforations.

26. The method of claim 25, wherein openings in said screens have diameters of about ⅖ to about one quarter the size of the minimum diameter of said catalyst beads in the reacting mixture.

27. The method of claim 25, wherein openings in said screens have diameters of about one third the size of the minimum diameter of said catalyst beads in the reacting mixture.

28. A method for manufacturing a polycarbonate, said method comprising:

reacting a dihydroxy compound with phosgene, a diphenyl carbonate, or a combination of phosgene and diphenyl carbonate, wherein said dihydroxy compound is manufactured with the apparatus of claim 1.

* * * * *